United States Patent

Pinchasik et al.

Patent Number: 5,620,457
Date of Patent: Apr. 15, 1997

[54] CATHETER BALLOON

[75] Inventors: Gregory Pinchasik; Jacob Richter, both of Ramat Hasharon, Israel

[73] Assignee: Medinol Ltd., Tel Aviv, Israel

[21] Appl. No.: 344,815

[22] Filed: Nov. 23, 1994

[51] Int. Cl.$^6$ .................................................. A61M 29/00
[52] U.S. Cl. ............................................. 606/194; 604/96
[58] Field of Search ............................ 606/191, 192, 606/194; 604/96–101; 623/1, 11, 12

[56] References Cited

U.S. PATENT DOCUMENTS

| | | | |
|---|---|---|---|
| 4,630,609 | 12/1986 | Chin | 606/194 |
| 4,950,227 | 8/1990 | Savin et al. | 623/1 |
| 4,983,167 | 1/1991 | Sahota. | |
| 5,226,889 | 7/1993 | Sheiban | 606/194 |
| 5,295,959 | 3/1994 | Gurbel et al. | 606/194 |
| 5,352,199 | 10/1994 | Tower. | |

FOREIGN PATENT DOCUMENTS

0552934A3  7/1993  European Pat. Off..

*Primary Examiner*—Michael Powell Buiz
*Assistant Examiner*—William W. Lewis
*Attorney, Agent, or Firm*—Kenyon & Kenyon

[57] ABSTRACT

A balloon catheter comprising a catheter tube, at least one inflatable balloon attached to the catheter tube and at least one narrowing device for narrowing the diameter of the at least one inflatable balloon at least at one portion.

6 Claims, 3 Drawing Sheets

CATHETER BALLOON

FIELD OF THE INVENTION

The present invention relates to balloon catheters generally.

BACKGROUND OF THE INVENTION

Balloon catheters are widely used for balloon angioplasty and stenting, to help keep a blood vessel or any other tubular body conduits open. For exemplary purposes only, the present invention will be described with respect to blood vessels as an example for any tubular body conduit suitable for balloon angioplasty and stenting.

Balloon angioplasty usually involves the insertion of the balloon catheter to the blood vessel. This procedure is usually followed by stenting, the insertion of a balloon catheter with a stent which is implemented in the blood vessel to prevent restonosis. The stent can be any suitable stent such as the stent described in Coassigned U.S. patent application Ser. No. 08/029,493, now abandoned. Typically, the balloon is inflated in a desired location in the blood vessel, thereby implementing the stent. Then the balloon catheter is deflated and pulled out of the blood vessel.

Prior art balloon catheters are usually tubular with a portion of the catheter capable of being inflated in a desired part of the blood vessel. The balloons of prior art balloon catheters are typically straight.

A drawback of prior art balloon catheters is their lack of flexibility. Usually, when a prior art balloon catheter is inserted, with or without a stent, into an arched blood vessel it reshapes the blood vessel such that it looses its arch like shape and becomes more rectangular. This loss of the arch-like shape may damage the blood vessel and may create undesired problems in the blood circulation.

SUMMARY OF THE INVENTION

It is therefore an object of the present invention to provide an improved balloon catheter.

The present inventors have realized that by using a balloon catheter which includes at least one narrowed portion, the balloon flexibility and therefore its capability to reshape itself according to the blood vessel shape increases.

There is thus provided, in accordance with a preferred embodiment of the present invention a balloon catheter comprising, a catheter tube, at least one inflatable balloon attached to the catheter tube, and at least one narrowing device for narrowing the diameter of the at least one inflatable balloon at least at one portion thereof.

Further, in accordance with a preferred embodiment of the present invention the narrowing device may be comprised essentially from the same material comprising the inflatable balloon or from a non-compliant plastic. Alternatively, the narrowing device may be comprised from a metal, such as coated or non-coated stainless steel, nickel and titanium alloys.

Further, in accordance with a preferred embodiment of the present invention, the narrowing device comprises a ring like shape narrowing device. The ring may be a zig-zagged ring capable of changing its diameter.

Further, in accordance with a preferred embodiment of the present invention, the diameter of the narrowing device is larger than the diameter of the catheter tube.

Additionally, in accordance with a preferred embodiment of the present invention, the diameter of the narrowing device and of the balloon are generally similar in a deflated position of the balloon and is smaller in an inflated position of the narrowing device.

There is also provided, in accordance with a preferred embodiment of the present invention, a method for fabricating a balloon catheter comprising the steps of providing a catheter tube and a balloon to be inflated in a portion thereof attached thereon, providing at least one narrowing device, placing the at least one narrowing device on predetermined positions of the balloon, and connecting the at least one narrowing device to the balloon.

Finally, there is also provided, in accordance with a preferred embodiment of the present invention a method for deploying a stent in a desired location comprising the steps of providing a stent, attaching the stent to a balloon catheter, guiding the balloon catheter to a desired location, inflating the balloon catheter in the location, and detaching the stent from the balloon catheter, wherein the stent and the balloon catheter are capable to shape in accordance with the shape of the location. The location may of any shape, such as in an arch like shape or in a generally non linear shape.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
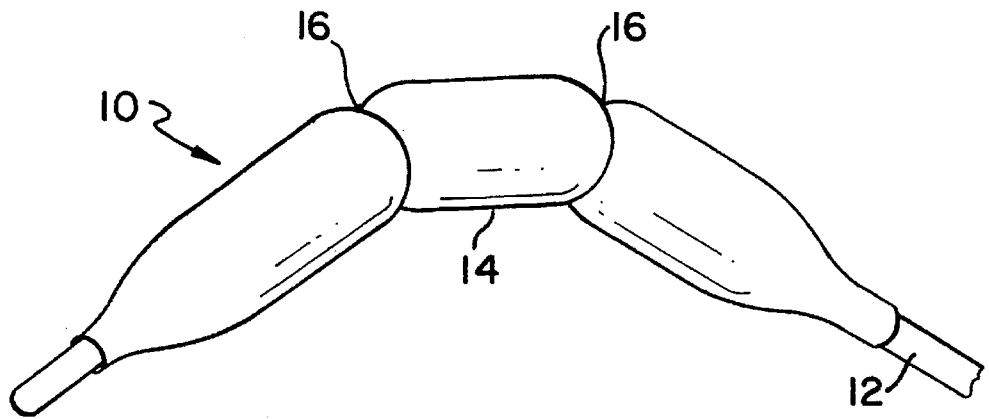
FIG. 1 is a schematic isometric illustration of a balloon catheter, constructed and operative in accordance with a preferred embodiment of the present invention.
Figure 2A:
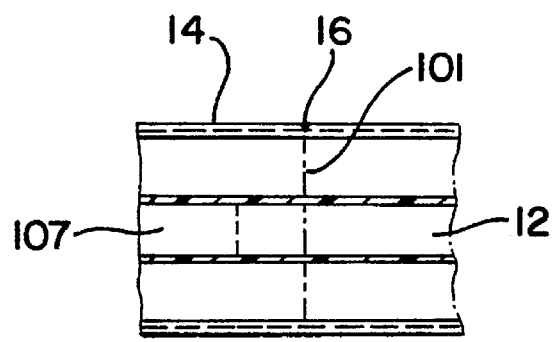
FIGS. 2A and 2B are schematic cross sectional illustrations of a portion of the balloon catheter of FIG. 1 in a deflated and inflated positions.
Figure 2B:
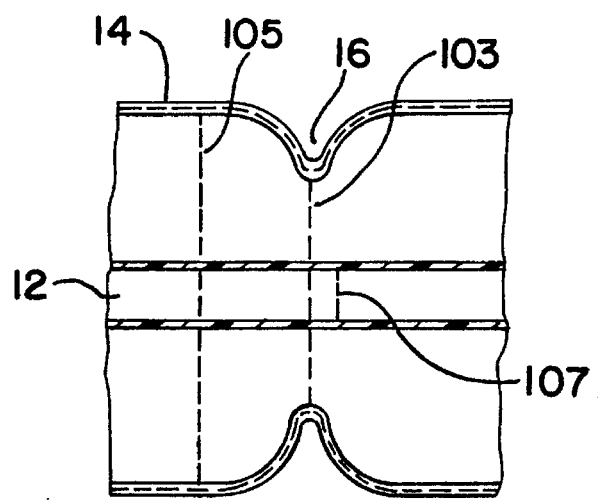

Reference is now made to FIGS. 1–2B which are schematic isometric illustrations of a balloon catheter and cross sectional illustrations of a portion thereof in deflated and inflated positions, respectively, constructed and operative in accordance with a preferred embodiment of the present invention.

The balloon catheter, generally referenced 10, preferably comprises a catheter tube 12, only part of which is shown here for simplicity, and a balloon 14 located on a portion of the catheter tube 12. The balloon 14 can be inflated and deflated by the surgeon which employs the balloon catheter.

It is a particular feature of the present invention that the diameter of the balloon 14 is not equal throughout. At last one narrowing device narrows the diameter periodically to form narrowed portions 16 thereof periodically such that the inflated balloon forms sausage like shapes.

It is a particular feature of the present invention that by narrowing periodically the diameter of the balloon, its flexibility and its ability to shape itself according to the shape of the blood vessel increases.

In the deflated position (FIG. 2A), the diameter of the balloon and of the narrowed portion 16 is preferably similar as indicated by the dashed line referenced 101. In the inflated position (FIG. 2B), the diameter of the narrowed portion 16 indicated by the dashed line referenced 103 is smaller than the diameter of the fully inflated areas of the balloon as indicated by the dashed line referenced 105.

According to one preferred embodiment of the present invention, the diameter 103 of the narrowed portions 16 of the balloon 10, are larger than the diameter of the catheter tube 12, indicated by the dashed line referenced 107.

It will be appreciated that the inflation of the balloon can be restricted by any suitable narrowing device, such as by a metal rings of the type that is acceptable to the human body or by using the material from which the balloon is made as described in more detail hereinbelow.

It will be appreciated that by determining the dimension and the diameter of the narrowing device, the degree of flexibility of the balloon catheter 10 can be determined. For example, if the diameter of the narrowing device is selected to be much smaller than the diameter of the balloon in its inflated position, i.e. a diameter which is generally similar to that of the catheter tube, a relatively high degree of flexibility is obtained.

It will be appreciated that by using the balloon catheter of the present invention, longer flexible stents can be used to support larger portions of blood vessels.

Figure 3A:
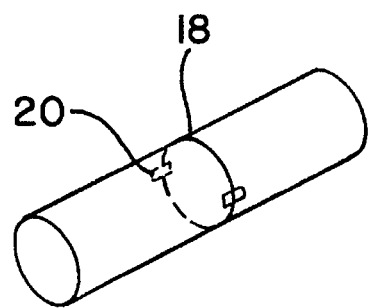
FIGS. 3A and 3B are schematic isometric illustrations of the balloon portion of the balloon catheter of FIG. 1 illustrating one type of a narrowing device, constructed and operative in accordance with a preferred embodiment of the present invention in a deflated and inflated positions, respectively.
Figure 3B:
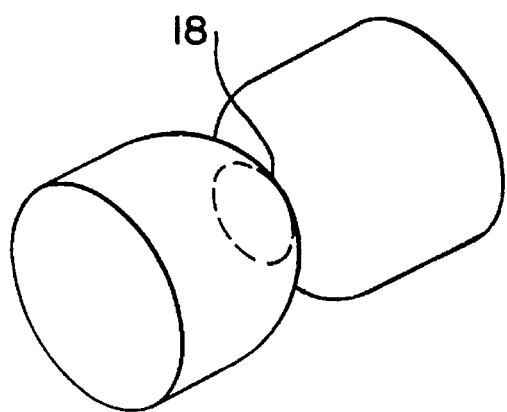
Figure 4A:
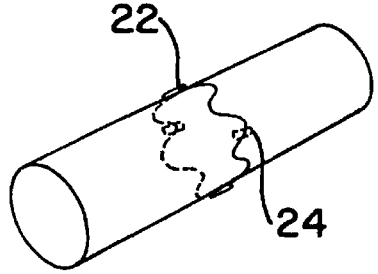
FIGS. 4A and 4B are schematic isometric illustrations of the balloon portion of the balloon catheter of FIG. 1 illustrating another type of a narrowing device, constructed and operative in accordance with a preferred embodiment of the present invention in a deflated and inflated positions, respectively.
Figure 4B:
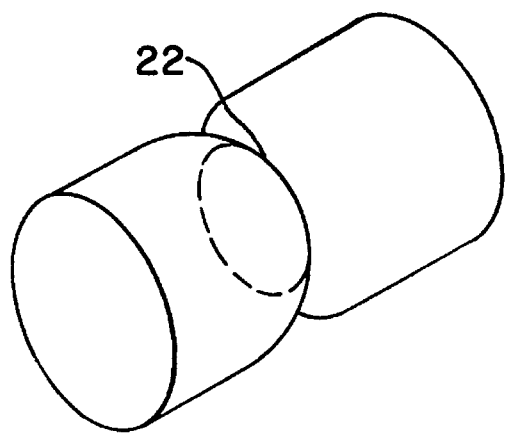

Reference is now made to FIGS. 3A–4B which are schematic isometric illustrations of the balloon 14 (the catheter tube 12 is not shown for simplicity) with two types of preferred narrowing devices 16. FIGS. 3A and 4B illustrate the balloon 14 in a deflated position and FIGS. 4B and 4B illustrate the balloon 14 in an inflated position.

Referring now specifically to FIGS. 3A and 3B, there is illustrated a narrowing device 18 in the form of a ring. The ring 18 may be any suitable ring which can be connected to the balloon itself by the connectors 20. The ring is preferably made of any suitable material such as from metal or from non compliant plastics. State of the art metal alloys which are used in stents implemented in blood vessels and which can be employed in the balloon catheter of the present invention include alloys of titanium and nickel and stainless steel with or without coating. Alternatively, the ring may be also made form the material from which the balloon is made, provided that its expansion is limited to the desired diameter of the narrowed portions of the balloon catheter.

Referring now specifically to FIGS. 4A and 4B, there is illustrated a narrowing device 22 in the form of a zig-zagged ring. The zig-zagged ring 22 may be any suitable ring which can be connected to the balloon itself by the connectors 24. It is a particular feature of the zig-zagged rings that they can change their diameter and therefore the diameter of the narrowing 16 can be adjusted as desired. The ring may be made from any of the materials used to form the ring 18.

A preferred method for fabricating the balloon catheter of the present invention preferably includes the following steps:

A. providing the catheter tube 12 and the balloon 14 to be inflated and connecting them in any conventional manner known in the art of balloon catheters fabrication. The balloon is typically connected near the edge of the catheter tube;

B. providing at least one narrowing device, such as the ring 18 of FIGS. 3A and 3B or the zig-zagged ring 22 of FIGS. 4A and 4B;

placing a desired number of narrowing devices on predetermined positions of the balloon 14; and connecting the narrowing devices to the balloon.

Figure 5:
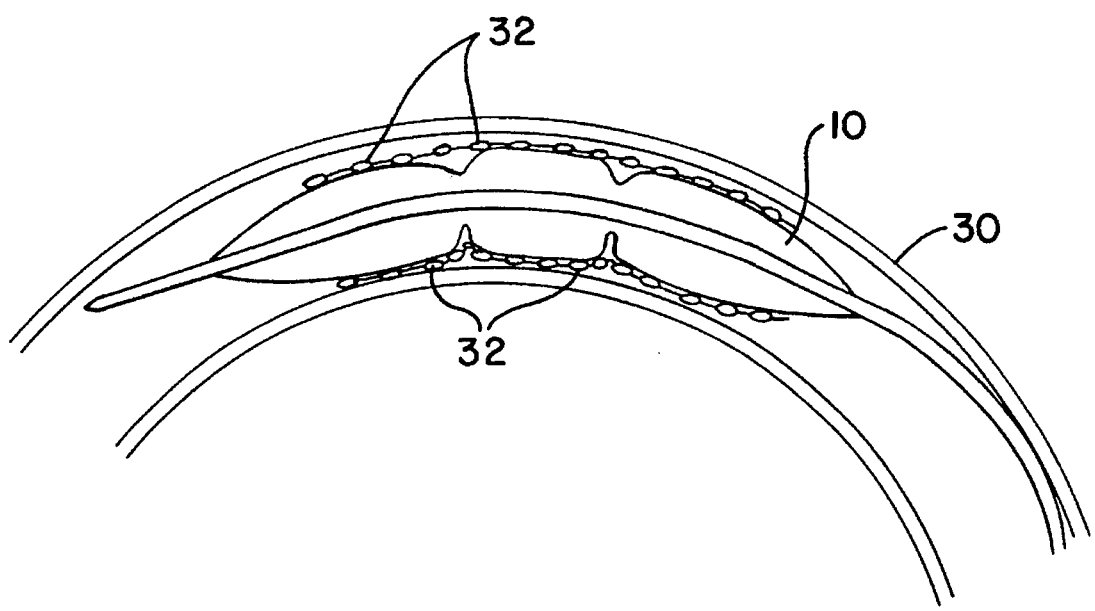
FIG. 5 is a schematic illustration of a balloon catheter, constructed and operative in accordance with a preferred embodiment of the present invention, and a stent connected thereto, in a deployment location of the stent.

Reference is now made to FIG. 5 which illustrates a balloon catheter, constructed and operative in accordance with a preferred embodiment of the present invention and a stent connected thereto in a deployment location of the stent. FIG. 5 illustrates a preferred method for deploying a stent in a desired location, such as in a blood vessel.

The method for deploying the stent in a desired location, such as in the arched blood vessel 30, preferably includes the following steps:

A. providing a stent schematically illustrated by the black dots connected therebetween and referenced 32, preferably a flexible one, such as the one described in Coassigned U.S. patent application Ser. No. 08/029,493;

B. attaching the stent to the balloon catheter 10 in any suitable manner such as the one described in Coossigned U.S. patent application Ser. No. 08/029,493;

C. guiding the balloon catheter 10 to the desired location in the arched blood vessel 30;

D. inflating the balloon catheter in the desired location; and

E. detaching the stent from the balloon catheter,

It will be appreciated that the balloon catheter 10 is shown in FIG. 5 in its inflated position.

The method of using the balloon catheter of the present invention is particularly useful when the stent 32 and the balloon catheter 10 are capable to shape in accordance with the shape of the shape of the blood vessel 30.

It is a particular feature of the present invention that the balloon catheter, with or without the stent, shapes itself according to the shape of the blood vessel rather than causing the blood vessel to reshape in accordance with the shape of the balloon catheter.

It will be appreciated that the preferred embodiments described hereinabove are described by way of example only and that numerous modifications thereto, all of which fall within the scope of the present invention, exist. For example, the narrowing device may be diagonal with respect to the longitudinal axis of the balloon. Another non-limiting example is that the narrowing devices can be connected therebetween.

It will be appreciated by persons skilled in the art that the present invention is not limited to what has been particularly shown and described hereinabove. Rather, the scope of the present invention is defined only by the claims that follow:

We claim:

1. A balloon catheter comprising:

a catheter tube;

at least one inflatable balloon attached to said catheter tube; and at least one ring-like shaped narrowing device for narrowing the diameter of said at least one inflatable balloon at least at one portion thereof; said narrowing device comprising a zig-zagged ring.

2. A balloon catheter according to claim 1 wherein said zig-zagged ring is capable of changing its diameter.

3. A method of fabricating a balloon catheter comprising the steps of providing a catheter tube;

providing an inflatable balloon having two ends;

attaching the two ends of the inflatable balloon to the catheter tube; and placing said at least one zig-zagged shaped narrowing device on predetermined positions of said balloon; and connecting at least one narrowing device to the balloon at predetermined positions between the attached ends of the inflatable balloon.

4. A method of deploying a stent in a desired location comprising the steps of:

providing a stent;

attaching said stent to a balloon catheter;

placing at least one zig-zagged shaped narrowing device on predetermined position of said balloon;

guiding said balloon catheter to a desired location;

inflating the balloon catheter is said location; and detaching the stent from said balloon catheter, wherein said stent and said balloon catheter are capable to shape in accordance with the shape of said location.

5. A method according to claim 4 wherein said location is in an arch like shape.

6. A method according to claim 4 wherein said location is generally not linear.

* * * * *